US Patent [19]  
Sengupta

[11] Patent Number: 4,514,330  
[45] Date of Patent: Apr. 30, 1985

[54] CARBON-7-SUBSTITUTED ATINOMYCIN D ANALOGUE

[75] Inventor: Sisir K. Sengupta, Needham, Mass.

[73] Assignee: Trustees of Boston University, Boston, Mass.

[21] Appl. No.: 508,689

[22] Filed: Jun. 28, 1983

[51] Int. Cl.$^3$ .......................................... C07C 103/52
[52] U.S. Cl. .......................................... 260/112.5 R
[58] Field of Search ................................ 260/112.5 R

[56] References Cited

PUBLICATIONS

J. Med. Chem. (1982) 25, 1214–1219.

Primary Examiner—Delbert R. Phillips
Attorney, Agent, or Firm—Paul J. Cook; Lawrence Gilbert

[57] ABSTRACT 7-(2,3-Epoxypropoxy)actinomycin D has been synthesized along with its major companion product, 7-(2,3-dihydroxypropoxy)-actinomycin D. They were characterized by UV-visible and CD spectra and by NMR studies. According to UV-visible absorptiometry, circular dichroism, and thermal denaturation studies, they bind to DNA in a manner that is comparable to actinomycin D. The analogues are, like actinomycin D, extremely cytotoxic to human lymphoblastic leukemic cells (CCRF-CEM) in vitro but are significantly less toxic than actinomycin D to normal $CDF_1$ mice in vivo. Unlike actinomycin, these analogues are metabolized in rats, and the metabolites are excreted in rat urine at a rapid rate. Compared to actinomycin D, the antitumor activity of the 7-(2,3-epoxypropoxy)actinomycin analogue against P-388 leukemia in mice is decidedly superior, and the therapeutic index is improved several fold.

2 Claims, 2 Drawing Figures

CARBON-7-SUBSTITUTED ATINOMYCIN D ANALOGUE

BACKGROUND OF THE INVENTION

This invention relates to new analogues of actinomycin D and to a method of preparing them.

Actinomycin D (AMD) is disclosed in German Pat. No. 1,172,680 and is a chromopeptide antibiotic whose potent activity in several tumors, including Wilm's tumor, gestational choriocarcinoma, and Kaposi's sarcoma, has been reported. It has the formula:

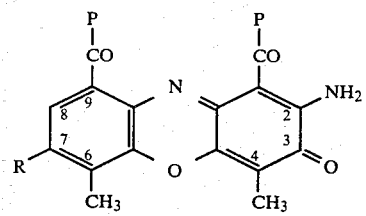

wherein P is

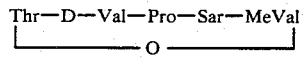

and R is hydrogen. AMD at submicromolar concentrations strongly inhibits DNA-dependent RNA synthesis and, to a lesser extent, DNA synthesis. Its interaction with DNA has been extensively studied, and the details of the mechanism of binding to DNA has been proposed, E. Reich, Cancer Res., 23, 1428 (1963), W. Muller and D. M. Crothers, J. Mol. Biol., 35, 251 (1968), and H. M. Sobell and S. C. Jain, J. Mol. Biol., 68, 21 (1972). It has been assumed that the cytotoxicity of AMD is due to its inhibition of RNA polymerase following the intercalative binding to DNA. It is quite possible, however, that the distortions in helical DNA resulting from the strong noncovalent association with AMD may not be solely responsible for the observed biological effects. For example, Nakazawa et al, J. Org. Chem., 46, 1493 (1981) suggest that an intermediate free-radical form of AMD may be the active form that causes DNA damage and cell death.

Furthermore, the proximal mechanism of biochemical action of AMD, which is evident from the inhibition of RNA synthesis, may not be the principal mechanism of selective cytotoxicity of the agent at the pharmacological level. For it is known that AMD is far more cytotoxic in those proliferating cells in which it inhibits DNA synthesis than in those of liver, kidney, muscle, etc., that are nonproliferating but are heavily dependent upon RNA synthesis for protein renewal.

Another pharmacological behavior of AMD is that it is not metabolized in vivo. Absence of metabolic conversion or detoxification of AMD leads to its accumulation in the cell nuclei of the host organs and causes cumulative toxicity. This acute cumulative toxicity limits the wide clinical application of AMD.

Accordingly, it would be desirable to snythesize new pharmacologically active analogues of AMD having increased drug efficacy. To achieve this, it would be desirable to increase the drug potency, by enhancing drug activity in the tumor cells and decrease toxicity to the host.

SUMMARY OF THE INVENTION

In describing this invention, the following notation as relates to the reactants and products produced by this invention is shown by Formula I.

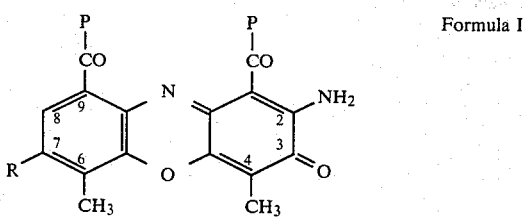

a, P = N(C$_2$H$_5$)$_2$
b, P = Thr—D-Val—Pro—Sar—MeVal

1, R = H
2, R = OH
3, R = OCH$_2$CH—CH$_2$
             \\__O__/
4, R = OCH$_2$CH(OH)CH$_2$OH
5, R = OCH$_3$

The compounds of Formula I which comprise the active compounds of this invention are those of Formula I which are compounds 3b and 4b. These compounds are prepared by reacting 7-hydroxyactinomycin (2b) with epibromohydrin under dry conditions in the presence of an alkali catalyst. The products then are recovered by filtration and chromatography.

DESCRIPTION OF SPECIFIC EMBODIMENTS

Figure 1:
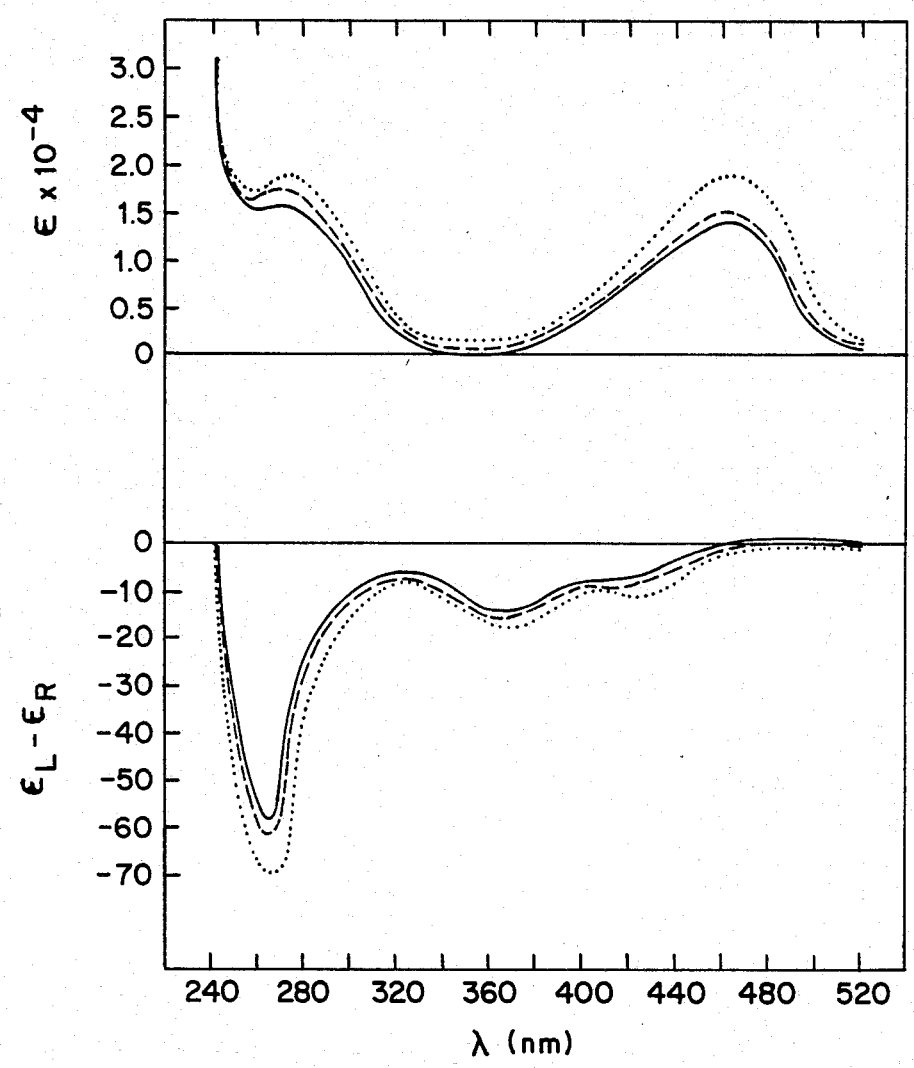
FIG. 1 shows the absorption (top) and circular dichroism (bottom) of compounds 3b, 4b and 5b.

As the first step, a systematic study of structure-antitumor activity relationship on the chromophore substituted actinomycin D analogues was done. A variety and a series of AMD analogues with substitutions at the C-7 and N$^2$ positions were synthesized and their biophysical, UV-visible absorptiometric, specific rotation, circular dichroic and NMR properties were determined. The purpose was to ensure that the integrity of the tricyclic phenoxazinone ring system as well as the conformation of the interannularly hydrogen-bonded pentapeptide lactone rings and the relationships between the chromophoric and the peptide lactones were unaltered from those of AMD. The analogues retained the biological activity in terms of inhibition of cellular nucleic acid synthesis also exhibited proportionate extracellular DNA-binding affinity. In a limited number of analogues, the DNA bindings were not only G-C base pair specific but also cooperative; i.e., the interaction of the chromophore and hydrogen bonding and hydrophobic interaction of the peptide lactone moieties with DNA were simultaneous. The experimental results established, among other things, that small alkoxy substituents, e.g., methoxy, ethoxy, and n-propoxy, at C-7 retained most of the above properties of AMD. The results discussed below clearly showed that the molecule of actinomycin D can accommodate a number of well-defined modifications at the C-7 and $N^2$ sites and still retain most of its physicochemical biophysical, biological and tumor-inhibitory properties.

7-(2,3-Epoxypropoxy)actinomycin D (3b) can be prepared from 7-hydroxyactinomycin D (2b). The initial synthetic investigations were carried out on the model 7-hydroxy analogue (2a). The chemical and spectral nature of these model analogues are very similar to the corresponding AMD analogues.

Mild reaction of epibromohydrin with 2a in dry acetone at 50°–55° C. in the presence of finely powdered anhydrous potassium carbonate yielded the alkylated products 3a and 4a. Similarly, AMD analogues 3b and 4b were obtained, starting from 7-hydroxyactinomycin (2b). Alkylation of 2 occurs entirely on the 7-hydroxy group, which is phenolic and is relatively less hindered compared to the alternative (tautomeric) 3-hydroxy group.

However, in the present case, alkylation of 2 with epibromohydrin yielded a major companion compound, 4, along with the desired product, 3. The companion compounds were readily identified as the 7-(2,3-dihydroxypropoxy) analogues 4a and 4b, respectively, in these series. They could be generated, alternatively, from 3 via mild acid-catalyzed hydrolysis of the epoxide ring. All these analogues were characterized by TLC, HPLC, UV and NMR properties and elemental analysis.

The structures of the model substituted compounds 3a and 4a, as well as AMD analogues 3b and 4b, could be easily verified by their NMR spectra. The NMR characteristics for the side-chain protons in model and AMD analogues are identical. In fact, the model analogues are of substantial help in assignment of appropriate chemical shifts in the complex and elaborate spectra of corresponding AMD analogues (See Table I).

consequence of the lack of the above-mentioned hydrogen bonding. Another long-range effect of the presence of hydrogen bonding in the 2-$NH_2$ group is reflected in the chemical shift of the 8-proton in AMD analogues. In the model series 1a, 3a and 4a, the 8-proton is located upfield (0.25–0.33 ppm) relative to AMD and analogues (1b, 3b and 4b). It should be pointed out that the analogues 3b and 4b have a new center of chilarity at the C-2 carbon.

The circular dichroic spectra of 3b and 4b in FIG. 1 show that 3b and 4b are almost identical in the electronic nature of the chromophores, as well as in the peptide conformations. In FIG. 1, absorption (top) and circular dichroism (bottom) spectra in 0.01 M phosphate buffer (pH7) containing EDTA ($10^{-5}$ M) and $Me_2SO$ (5%): 3b (...), 4b (---), 5b (—). Concentration of drug in each case was $1.0 \times 10^{-5}$ M. In this respect, they are almost indistinguishable from the known analogue 7-methoxyactinomycin D (5b), whose structure and physical properties we have previously reported. The absorption spectra of all these analogues in aqueous buffer are also almost superimposable. The differences in the extinction values in the absorption spectra between the analogues 3b and 4b and 7-methoxyactinomycin D (5b) are simultaneously exhibited in the CD spectra of the respective analogues. The absorption spectrum of the analogues above 240 nm is mainly due to the electronic configuration of the tricyclic chromophore. The CD spectrum in the same wavelength region is an indicator of peptide conformation in actinomycin analogues, because it is the peptide lactone ring that confers optical activity on the nearly planar chromophore. The nature of the CD spectra (3b, 4b and 5b) asserts that in these analogues there is an identical relationship between the chromophores and peptide lactones. This relationship is very important, because during binding

TABLE I

Comparison of NMR Chemical Shifts in the Chromophore Ring Protons and C-7 Substituents in Actinomycin D and Analogues and Model Derivatives[a]

| Compd | 7-H[b] | 8-H[b] | 2-$NH_2$[b] | 4-$CH_3$[b] | 6-$CH_3$[b] | Ar$OCH_2$[c] | 2-H[c] | 3-H[c] | 2-OH, 3-OH[c] |
|---|---|---|---|---|---|---|---|---|---|
| 1B | 7.53 | 7.63 | 7.08 | 2.24 | 2.67 | | | | |
| 3b | | 7.21 | 7.09 | 2.24 | 2.41 | 3.70–4.14 | 3.49 | 2.62–2.87 | |
| 4b | | 7.26 | 7.08 | 2.24 | 2.45 | 3.72–4.13 | 3.53 | 2.65–2.90 | 4.16–4.24 |
| 1a | 7.17 | 7.38 | 5.61 | 2.30 | 2.53 | | | | |
| 3a | | 6.89 | 5.39 | 2.28 | 2.39 | 3.88–4.28 | 3.41 | 2.72–3.00 | |
| 4a | | 6.93 | 5.39 | 2.28 | 2.41 | 3.88–4.24 | 3.41 | 2.70–2.96 | 4.20–4.28 |

[a]90-MHz spectrum of $CDCl_3$ solution, chemical shifts in parts per million ($\delta$) to low field from internal tetramethylsilane.
[b]These protons are present in the chromophoric rings of AMD and model analogues.
[c]These protons are part of the substituent chains at C-7 of the synthetic analogues 3a, b and 4a, b.

Furthermore, the effects of the substituents at C-7 on the NMR chemical shifts of the vicinal proton in both the model and AMD chromophores are similar. The 8-H and 6-$CH_3$ signals are shifted upfield, as a result of alkoxy substitution at C-7, with no apparent effect on the 4-$CH_3$ proton shifts. The 2-$NH_2$ protons in the model analogues (1a, 3a and 4a) behave differently from the corresponding AMD analogues (1b, 3b and 4b). In AMD and analogues, the 2-$NH_2$ protons are hydrogen bonded with $\beta$-threonine-NH, as well as the actinocyl carbonyl oxygen, resulting in a downfield shift (7.08–7.09 ppm) compared with the 2-amino protons in the model analogues (5.61–5.39 ppm). This strong hydrogen bonding in AMD also stabilized the 2-$NH_2$ protons from the long-range inductive effect of 7-substitution in AMD analogues 3b and 4b but not in the model derivatives. In 1a, 3a and 4a, these protons are found to be shifted relatively upfield (from 5.61 to 5.39 ppm) as a to DNA, AMD and some analogues are known to rely on the cooperative role between the chromophore and the peptide lactones for their highly specific DNA-binding property.

Figure 2:
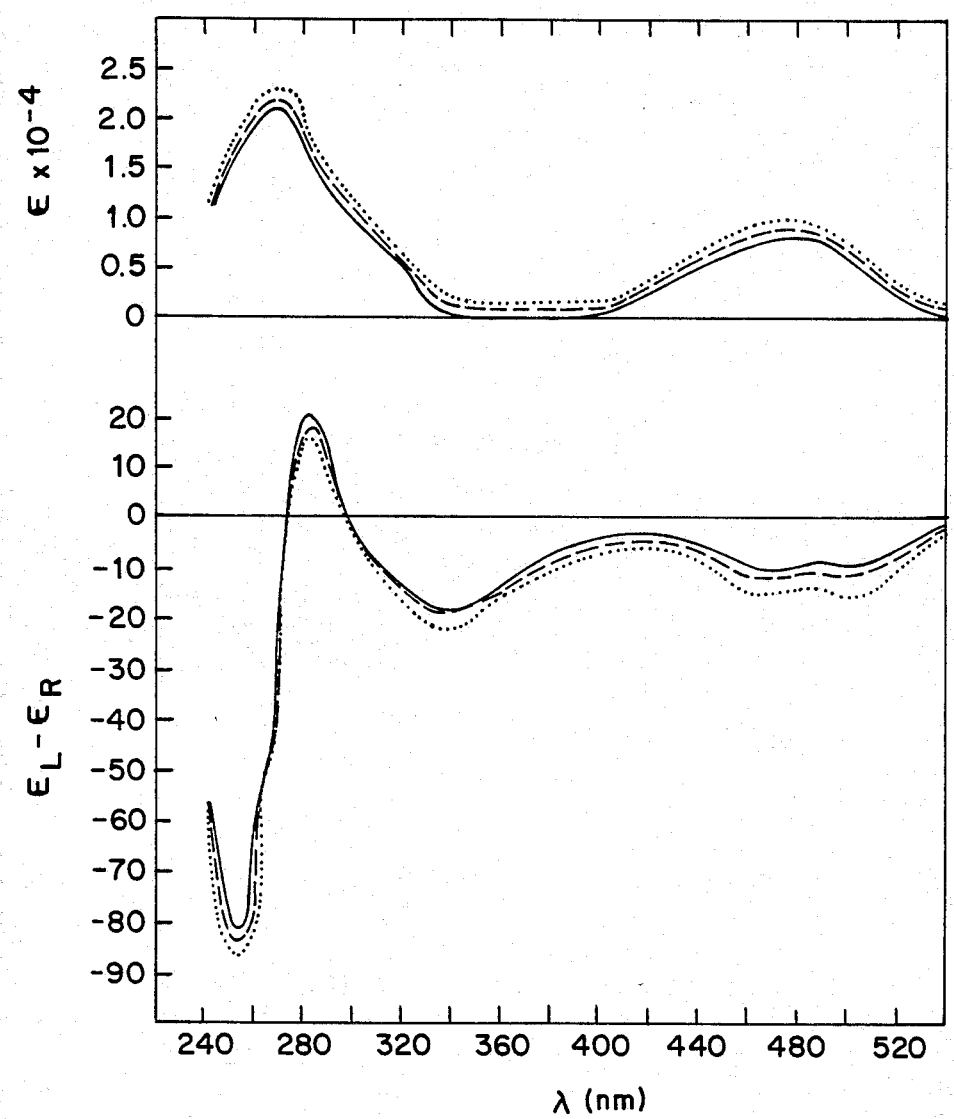
FIG. 2 shows the absorption (top) and CD spectra (bottom) of the DNA (P)-drug complex for compounds 3b, 4b and 5b.

Any change in the configurations of the peptide lactones on binding to DNA is generally expressed in the CD spectra of the analogue-DNA complexes. Simultaneously, the change in the electronic configuration of the chromophore is exhibited by the bathochromic and hypochromic shifts of the visible absorption maximum of the chromophore. The changes in the visible absorption spectra of 3b, 4b and 5b and also their CD spectra observed after adding calf thymus DNA [mole ratio of DNA (P)/analogue=10:1] are identical (FIG. 2). In FIG. 2, the absorption (top) and CD spectra of the DNA (P)-drug complex (ratio 10:1). Concentrations, buffer and line types are as in FIG. 1.

The analogues, i.e., 7-nitro- and 7-aminoactinomycin D, bind to DNA in exactly the same way as AMD, i.e., by intercalation of the chromophore and concomitant hydrogen and hydrophobic interactions of the peptide lactones. The similarity of these characteristics in the absorption and CD spectra of 3b, 4b and 7-methoxyactinomycin D (5b) with those of AMD strongly suggests similar DNA-binding modes.

Thermal denaturation studies were carried out according to the procedure described in J. Med. Chem., Vol. 24, p. 1052 (1981). The $\Delta T_m$ values in Table II give a measure of stabilization of DNA helical structure as a consequence of drug binding.

TABLE II

Effect of Actinomycin D Analogues and Model Derivatives on $T_m$ of DNA. In Vitro Growth-Inhibitory Activity

| compound | $T_m$, a°C. | in vitro (CCRF-CEM)[b] ID$_{50}$, ng/mL |
|---|---|---|
| 1b | 7.1 ± 0.15 | 60 |
| 2b | 6.7 ± 0.15 | 950 |
| 3b | 6.0 − 4.3[c] | 9.0 |
| 4b | 5.1 ± 0.15 | 85 |
| 1a, 2a, 4a | 0 | ~10 × 10$^{3d}$ |
| 3a | 0 | ~9000 |

[a]$\Delta T_m = T_m$ of DNA-drug complex minus $T_m$ of DNA. Concentraiton of drug, 1.4 × 10$^{-4}$ M; of DNA (P), 1.4 × 10$^{-3}$ M in 0.01 M phosphate buffer (pH 7.0), 5 × 10$^{-3}$ M in EDTA and 5% dimethyl sulfoxide.
[b]Using human lymohoblastic leukemia cells in logplastic growth. Compounds were dissolved in Me$_2$So medium, final growth medium contained 1% Me$_2$SO.
[c]The DNA-melting curves, i.e., change in the OD at 259 nm due to the separation of strands in the DNA double helix, was not smooth and uniform in this instance, indicating major changes in the DNA strand due to drug interaction during the experiment. This is quite different from the very uniform and smooth changes of OD at 259 n, observed with other analogues.
[d]Highest dose tested.

These values are derived at high temperature (67°–75° C.) and may not always correlate with the results of other DNA-binding studies (e.g., absorptiometric or circular dichroic). The $\Delta T_m$ data for the AMD analogues show that binding of all these analogues to the double helices of DNA effect an almost uniform stabilization, except for 3b, which gives a very broad and sometimes erratic $\Delta T_m$ value, possibly as a result of alkylation and covalent binding and scission of the DNA chain. In 3b, when it is bound to DNA, the active epoxy function may cause DNA fragmentation at the high temperature of the experiment. The compounds 1a–4a do not appear to bind to DNA (either by $T_m$ or by absorption spectra). The broad melting profile of the 3b-DNA complex compared with the sharp and smooth profiles for the melting profiles of 1b, 2b and 4b complexes of DNA is an indirect evidence for covalently bound 3b with DNA.

The analogues were assayed for in vitro growth-inhibitory activity against human lymphoblastic leukemic cells (CCRF-CEM) in the log phase, and the results are reported in Table II. The assay is highly sensitive for AMD and its analogues, and it provides relative cytotoxicity values for these agents.

Table II shows that 3b is about sevenfold more cytotoxic and 4b is about 1.5 times less cytotoxic than AMD. In comparison, the model analogues 3a and 4a are more than 1000-fold less toxic compared to AMD and its analogues. It appears that the epoxy function alone does not account for the extraordinary high cytotoxicity of 3b. The model analogue, 3a, cannot function as a potent growth-inhibitory agent (ID$_{50}$=9 μg/mL) when it is a derivative of 1a, because 1a has no DNA-binding related activity. This does not imply that the epoxy group in 3b has no substantial contribution in the biological activity of this analogue. In fact, it does, and the final biological activity of 3b is a combination of two important factors, the integrity of the active form of actinomycin and the substituent epoxy group that happens to be of the right size and is placed at the right position of AMD in order to retain the DNA-binding property.

Studies on in vivo activity of AMD and AMD analogues were carried out with P-388 lymphocytic leukemia in CDF$_1$ hybrid mice. The drugs were administered either daily for 4 successive days (qd 1–4) or on days 1, 5 and 9 (q4d 1, 5, 9) beginning 1 day after tumor implantation.

Table III shows the results obtained on schedules q4d 1, 5, 9.

TABLE III

Effects of AMD and Chromophore Substituted AMD Analogues on CDF$_1$ Mice with P-388 Leukemia (Survival and Cure)[a]

| compound | dose, mg/kg | MST,[b] days | % ILS[c] | cure[d] |
|---|---|---|---|---|
| no drug | | 11.0 | | 0/15 |
| 1b | 0.031 | 13 | 18 | 0/7 |
| | 0.062 | 16 | 45 | 1/7 |
| | 0.125 | 26 | 136 | 0/7 |
| | 0.250 | 17 | 55 | 0/7 |
| | 0.375 | 9 | | |
| 2b | 0.15 | 12 | 10 | 0/7 |
| | 0.30 | 17 | 55 | 0/7 |
| | 0.60 | 21 | 89 | 0/7 |
| | 1.20 | 25 | 127 | 0/7 |
| | 1.80 | 26 | 136 | 0/7 |
| | 3.00 | 15 | 37 | 0/7 |
| 3b | 0.15 | 29 | 164 | 0/7 |
| | 0.30 | 40 | 263 | 1/7 |
| | 0.60 | 41 | 255 | 1/7 |
| | 1.20 | 43 | 291 | 3/7 |
| | 1.80 | 44 | 300 | 3/7 |
| | 2.40 | 26 | 136 | 2/7 |
| 4b | 0.15 | 16 | 45 | 0/7 |
| | 0.30 | 20 | 82 | 2/7 |
| | 0.60 | 25 | 136 | 1/7 |
| | 1.20 | 32 | 191 | 0/7 |
| | 1.80 | 15 | 36 | 0/7 |

[a]Male CDF$_1$ (18–23 g) mice were inoculated intraperitoneally (ip) with 10$^6$ P-388 cells on day 0. Drugs were administered, also ip, in 10% dimethyl sulfoxide-saline on days 1, 5 and 9. Test solutions were kept at 0–4° C., protected from light, and the stability and homogeneity were checked periodically by TLC and HPLC.
[b]MST = median survival time.
[c]% ILS = percent increase in life span.
[d]Over 55 day survivors. Average of three experiments.

The analogues 3b and 4b at their optimal nontoxic dose levels demonstrate, respectively, about a 2.5- and 1.5-fold increase in survival time over AMD (1b) or 7-hydroxyactinomycin D (2b). The compounds 1b and 2b are approximately equiactive in respect of % ILS, although 2b needs an over 14-fold higher dose than AMD to effect the equiactivity. In fact, for optimum activity, all the analogues need several fold higher level doses than AMD; therefore, the homogeneity of all the test solutions were ascertained carefully by TLC and HPLC each time the agents were tested. In this test system, compound 3b shows activity that is superior to AMD in many respects. Its dose-response curve is very broad, as opposed to AMD's dose-response curve, which is very narrow. Additionally, 3b produces long-term survivors throughout this dose range. Furthermore, at optimal dose ranges of 1.2 and 1.8 mg/kg, it produces cure (tumor free) in three out of seven treated animals.

The therapeutic indexes of both 3b and 4b in qd 1–4 and q4d 1, 5, 9 schedules of treatment are calculated and expressed in Table IV. Both analogues are demonstrated to be transformed in vivo to highly polar metabolites, all of these in the form of conjugates of 4b. These and other unidentified polar metabolites are excreted at about two to three times the rate of AMD in rat urine. This process of in vivo metabolic transformation and fast excretion appears to play a major role in reducing the in vivo toxicity factor of 3b and 4b. A lack of these properties in AMD is known to cause acute and cumulative toxicity in patients.

Furthermore, 3b is an agent that has an alkylating function, i.e., the epoxy group, and also the elements of the actinomycin molecule that contribute to it DNA-binding affinity. Combination of these two attributes in the structure of 3b may probably also contribute to its efficiency as a DNA alkylating agent in highly proliferating cells.

A molecule like 3b is a valuable probe for many biochemical and biological studies. It has a DNA-binding property that is closely parallel to AMD at ambient temperature. It also can bind covalently to DNA at higher temperatures (37° C. or higher) or with a longer period of incubation (~20 h).

TABLE IV

Comparison of AMD with Chromophore Substituted AMD Analogues vs. P-388 Leukemia[a]

| drug | MED[b] 3 | MED[b] 4 | MTD[c] 3 | MTD[c] 4 | therapeutic index: MTD/MED 3 | therapeutic index: MTD/MED 4 |
|---|---|---|---|---|---|---|
| 1b | 0.0625 | 0.05 | 0.25 | 0.15 | 4 | 3 |
| 2b | 0.275 | 0.2 | 4.2 | 2.0 | 15 | 10 |
| 3b | 0.05 | 0.0375 | 3.6 | 1.6 | 72 | 43 |
| 4b | 0.15 | 0.125 | 1.8 | 1.4 | 12 | 6 |

[a]Drugs administed ip once daily either for 4 successive days (qd 1–4) or on days 1, 5 and 9 (q4d 1, 5 9), starting 1 day after tumor implantation.
[b]MED (minimum effective dose) is the dose (milligrams/kilogram) providing an increase in life span of 40% over control in P-388 tumor-bearing mice.
[c]MTD (maximum tolerated dose) is the lethal dose (milligrams/kilogram) for 10% normal CDF$_1$ male mice (18–23 g); animals observed for deaths during 21 days (LD$_{10}$ = 21 days). Values were calculated from a plot of log dose vs. percent mortality. Average of two to three experiments.

The following example illustrates the present invention and is not intended to limit the same.

EXAMPLE I

Melting points were obtained with a Thomas-Hoover melting point apparatus at a heating rate of 2° C./min. Column chromatography was accomplished with silica gel powder (Baker No. 3405, 60–20 mesh) or acid alumina (Woelm grade 1). Limited gel-filtration work was done on Sephadex LH-20, particle size 25–100 μm (Pharmacia Fine Chemicals). Thin-layer chromatography was performed on silica gel plates (E. M. Laboratories, Inc.). Solvent systems used were (A) butanol-formic acid-H$_2$O (75:13:12), (B) EtOAc-acetone (3:1), and (C) Cifferri, the organic phase of the mixture EtOAc-MeOH-H$_2$O (20:1:20). High-performance liquid chromatography was carried out on a Varian Model 5020 gradient liquid chromatograph equipped with CD-111L chromatography data system and fitted with Varian reversed-phase C$_{18}$ column with isocratic solvent systems, CH$_3$-CN-5 mM NH$_4$OAc buffer, pH 6.4 (68:32 or 62:38), pressure 80–140 atm, flow rate 1.5 mL/min, with UV-visible variable and fixed wavelength dual detectors at 254 and 466 nm. Spectra were determined on the following instruments: IR spectra were obtained with a Perkin-Elmer Model 237 Infra Cord with KBr micropellets or chloroform solutions; UV-visible spectra were obtained on a Gilford 250 spectrophotometer, which, with the addition of a base-line reference compensator (Analog Multiplexer 6064) and thermoprogrammer, auto four cell programmer and thermoelectric cell holder 2577, was used to obtain thermal denaturation curves; NMR spectra were obtained on a JOEL FQ-90-90MHZ spectrometer equipped with Fourier transform; and CD spectra were obtained on a Cary 61 spectrophotometer. All elemental analyses were within ±0.4% of the theoretical values. Actinomycin D, batch no. NCS 3053, lot L554651-0-10, was provided by Natural Products Branch, National Cancer Institute, Silver Spring, Md. Calf thymus DNA type 1 was purchased from Sigma Chemical Co.

7-(2,3-Epoxypropoxy)-(3b) and 7-(2,3-Dihydroxypropoxy) actinomycin D (4b). General Method. 7-Hydroxyactinomycin D (2b, 17 mg, 01013 mmol) and powdered anhydrous potassium carbonate (8.5 mg) were placed in a tube containing a magnetic stir bar. After addition of dry acetone (4.2 mL) and epibromohydrin (170 μL), the tube was purged with N$_2$ and stoppered. The mixture was stirred at 50°–55° C. for 16 h; the color of the solution turned from purple to orange when the reaction was complete. Filtration, followed by evaporation under N$_2$, gave an oily residue, which was chromatographed on a silica gel plate (solvent system B). Two major bands were obtained. The faster moving band (R 0.39, TLC, solvent B) upon elution with acetone yielded 3.7 mg (20.2%) of pure red solid (3b): mp 265°–267° C. dec; UV $\lambda_{max}$ (CHCl$_3$) 464 nm (ε 20 100); $[\alpha]^{22}_D$ −406±20° (c 0.1, CHCl$_3$); HPLCt$_R$ 15.3 min vs. 17.6 min for 7-methoxyactinomycin D. Anal. (C$_{65}$H$_{90}$N$_{12}$O$_{18}$·2H$_2$O) C,H,N.

The slower moving band (R 0.28, TLC, solvent system B) yielded 7.4 mg (42.8%) of orange solid 4b: mp 285° C. dec; UV $\lambda_{max}$ (CHCl$_3$) 464 nm (ε 19 470); $[\alpha]^{22}_D$ −308±20° (c 0.1, CHCl$_3$); HPLCt$_R$ 7.5 min vs. 9.3 min for AMD (CH$_3$CN-5mM NH$_4$OAc, 62:38, 1.5 mL/min). Anal. (C$_{65}$H$_{92}$N$_{12}$O$_{19}$·3H$_2$O) C,H,N.

Compound 3a: mp 225°–227° C.; UV $\lambda_{max}$ (CHCl$_3$) 466 nm (ε 22 100); TLC R 0.62 (solvent system B); yield 41%. Anal. (C$_{27}$H$_{34}$N$_4$O$_6$) C,H,N.

Compound 4a: mp 198°–202° C.; UV $\lambda_{max}$ (CHCl$_3$) 467 nm (ε 18 500); TLC R 0.43 (solvent system B); yield 30%. Anal. (C$_{27}$H$_{36}$N$_4$O$_7$) C,H,N.

Conversion of Compound 3b to 4b. Compound 3b (2 mg) in 1 mL of tetrahydrofurane was treated with 50 μL of 25% aqueous perchloric acid and let stand at 22° C. for 3 h. The solution was diluted with water (1 mL) and extracted with ethyl acetate (5×5 mL). The washed and dried extract was applied on TLC (solvent B), which separated compound 4b, R 0.29 (65%), from 15% of compound 3b, R 0.40, which remained unconverted. Compared with authentic samples by TLC solvent systems A-C, HPLC, and IR (KBr).

Compound 3b: R 0.32 (solvent system A), 0.28 (solvent system C).

Compound 4b: R 0.49 (solvent system A), 0.13 (solvent system C).

Biological Experiments. Determination of LD$_{10}$ Values. Tumor-free CDF$_1$ male mice weighing 18–23 g were given a broad range of doses of drugs in 10% dimethyl sulfoxide-saline on either days 1, 5 and 9 or on 4 successive days. Drugs were administered intraperitoneally (ip).

The maximum tolerated doses of AMD and analogues that caused deaths in only 10% of the tested animals in 21 days were recorded as MTD. The results are an average of two experiments in each. The MTD values obtained following schedules q4d 1, 5, 9 (three injections) and qd 1-4 (four injections) are recorded in Table IV. These doses are the same as $LD_{10}$ (lethal dose of 10% of tumor-free animals in 21 days).

The results show that on a q4d 1, 5, 9 schedule, MTd doses are 14-fold for 3b, 7-fold for 4b and 17-fold for 2b of the MTD dose for AMD. Similarly, on the qd 1–4 schedule, 3b is 11-fold, 4b is 9-fold and 2b is 13-fold less toxic than AMD.

In an additional experiment, two animals at $LD_{10}$ (or MTD) dose levels were sacrificed on day 14, and the organ sections from these animals were evaluated for gross pathology in the following way. Organs, e.g., spleen, liver, kidney, large and small intestine, heart, lung, pancreas and adrenals, were removed and fixed in 10% natural buffer formalin. They were kept immersed for 2 weeks; tissues were dehydrated through graded alcohols (70, 90, 95 and 100%), cleared in cedarwood oil and embedded in paraffin. Sections were cut in 7 μm and mounted with gelatin on microscope slides. After drying, sections were stained with Mayer's hematoxylin and eosin and examined with light microscopy.

The sections of spleen showed haematopoiesis indicative of bone-marrow toxicity for all the analogues, as well as AMD. However, in other organs, e.g., liver, kidney, large and small intestines, heart, lung, pancreas or adrenals, no observable toxic effects were in evidence.

I claim:

1. The compound 7-(2,3-epoxypropoxy)actinomycin.
2. The compound 7-(2,3-dihydroxypropoxy)actinomycin.